(12) United States Patent
Chen

(10) Patent No.: US 6,749,181 B1
(45) Date of Patent: Jun. 15, 2004

(54) HUMIDIFIER

(75) Inventor: Shih-Yen Chen, Yung Kang (TW)

(73) Assignee: Fong Yen Electrical Co., Ltd., Tainan Hsien (TW)

( * ) Notice: Subject to any disclaimer, the term of this patent is extended or adjusted under 35 U.S.C. 154(b) by 34 days.

(21) Appl. No.: 10/300,632

(22) Filed: Nov. 21, 2002

(51) Int. Cl.⁷ ................................................ B01F 3/04
(52) U.S. Cl. ...................... 261/66; 261/72.1; 261/119.1
(58) Field of Search ........................... 261/38, 66, 72.1, 261/73, 119.1, 142, DIG. 65

(56) References Cited

U.S. PATENT DOCUMENTS

| 3,131,237 A | 4/1964 | Collins, Jr. ................. 261/153 |
| 6,164,630 A | 12/2000 | Birdsell et al. ............ 261/18.1 |
| 6,176,473 B1 | 1/2001 | Stanek et al. ................. 261/26 |
| 6,338,473 B1 | 1/2002 | Hebblewhite et al. ... 261/119.1 |

*Primary Examiner*—Scott Bushey
(74) *Attorney, Agent, or Firm*—Rosenberg, Klein & Lee

(57) ABSTRACT

An improvement on a humidifier includes a leakage prevention ring, and two opposite supporting plates. The leakage prevention ring has several ring-shaped portions, which define inner and outer concentric annular trenches. The concentric trenches are closely mounted onto an upper end of a vapor conduit, and a down-projecting annular protrusion of a vapor outlet disposed right above the conduit respectively. The supporting plates can pivot up and down, and are biased by torsion springs to hold a water-supplying bottle between them in an inverted vertical position, which is connected to a valve of the humidifier, so that the bottle can't tilt or shake to cause damage to the valve.

4 Claims, 7 Drawing Sheets

HUMIDIFIER

BACKGROUND OF THE INVENTION

1. Field of the Invention

The present invention relates to a humidifier, more particularly a humidifier, which can prevent vapor from leaking through a joint between a conduit and a vapor outlet thereof, and which provides a supporting mechanism for increasing stability of a water-containing bottle connected thereto.

2. Brief Description of the Prior Art

Humidifiers are used for maintaining proper amount of humidity in the air for the well being of humans.

Referring to FIG. 1, a conventional humidifier includes a main body 1, a valve 12, a vapor conduit 14, and an upper cover 15. The main body 1 includes a heating member (not shown), a holding space 11, and a water tank in a lower section of the main body 1. The valve 12 is disposed in the holding space 11, and is provided for controlling flow of water from a bottle to the main body 1. The conduit 14 is disposed in the main body 1 for vapor to pass through. The upper cover 15 is joined to the upper end of the main body 1. The upper cover 15 has a vapor outlet 17, which is connected to the upper end of the conduit 14, has and a through hole 16, which is right above the valve 12.

A water-containing bottle (not shown) is passed through the hole 16, and connected to the valve 12 at a neck in an inverted position for supplying the humidifier with water.

Thus, vapor produced by the humidifier can travel through the vapor outlet 17 via the conduit 14 to increase humidity in the air. However, the humidifier is found to have disadvantages as follows:

1. The vapor outlet 17 is simply mounted around the upper end of the conduit 14 or the upper end of the conduit is simply mounted around the lower end of the outlet 17 without leakage prevention means being provided. Consequently, vapor is prone to leak through the joint between the conduit 14 and the vapor outlet 17 thereof
2. The valve 12 is subject to damage because the water-containing bottle connected thereto is likely to tilt or shake due to lack of supporting means.

SUMMARY OF THE INVENTION

It is a main object of the present invention to provide a humidifier, which is equipped with a leakage prevention means on a joint between a conduit and a vapor outlet thereof to prevent vapor from leaking.

It is another object of the present invention to provide the humidifier with a supporting means for increasing stability of a water-supplying bottle connected to a valve thereof.

The leakage prevention means of the humidifier of the present invention has several ring-shaped portions, which define inner and outer concentric annular trenches. The concentric trenches are respectively closely mounted onto an upper end of a vapor conduit, and a down-projecting annular protrusion of a vapor outlet disposed right above the conduit. The supporting plates can be pivoted up and down, and are biased by torsion springs to hold the water-supplying bottle in between in an inverted vertical position, which is connected to a valve of the humidifier. The torsion springs will keep the supporting plates in a sloping position with certain resistance if a bottle connected to the valve has such a circumference that the supporting plates are pivoted away from the usual horizontal position by the bottle.

BRIEF DESCRIPTION OF THE DRAWINGS

The present invention will be better understood by reference to the accompanying drawings, wherein.

DETAILED DESCRIPTION OF THE PREFERRED EMBODIMENTS

Figure 1:
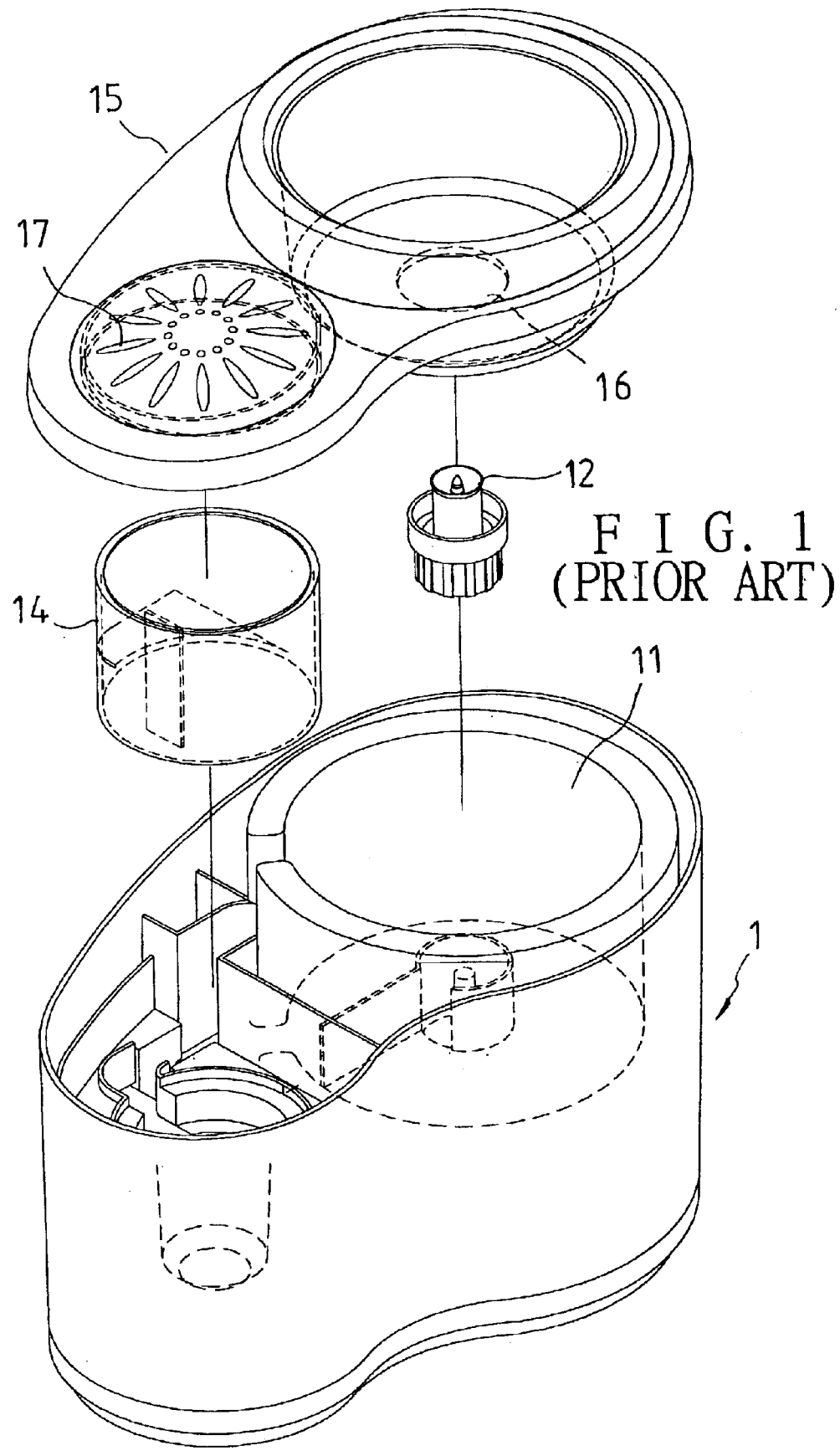
FIG. 1 is an exploded perspective view of the conventional humidifier as described in the Background.
Figure 2:
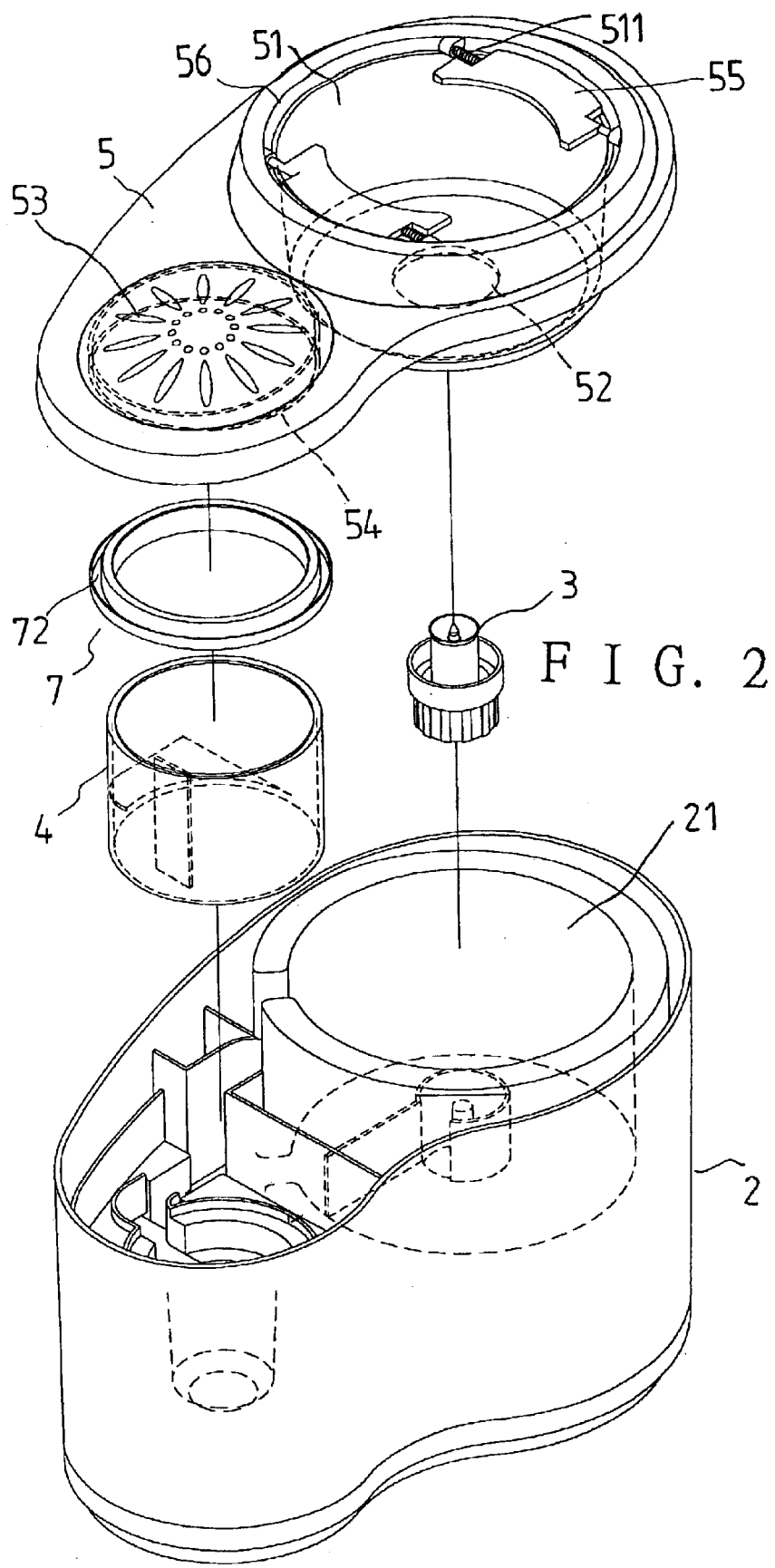
FIG. 2 is an exploded perspective view of the humidifier according to the present invention.
Figure 3:
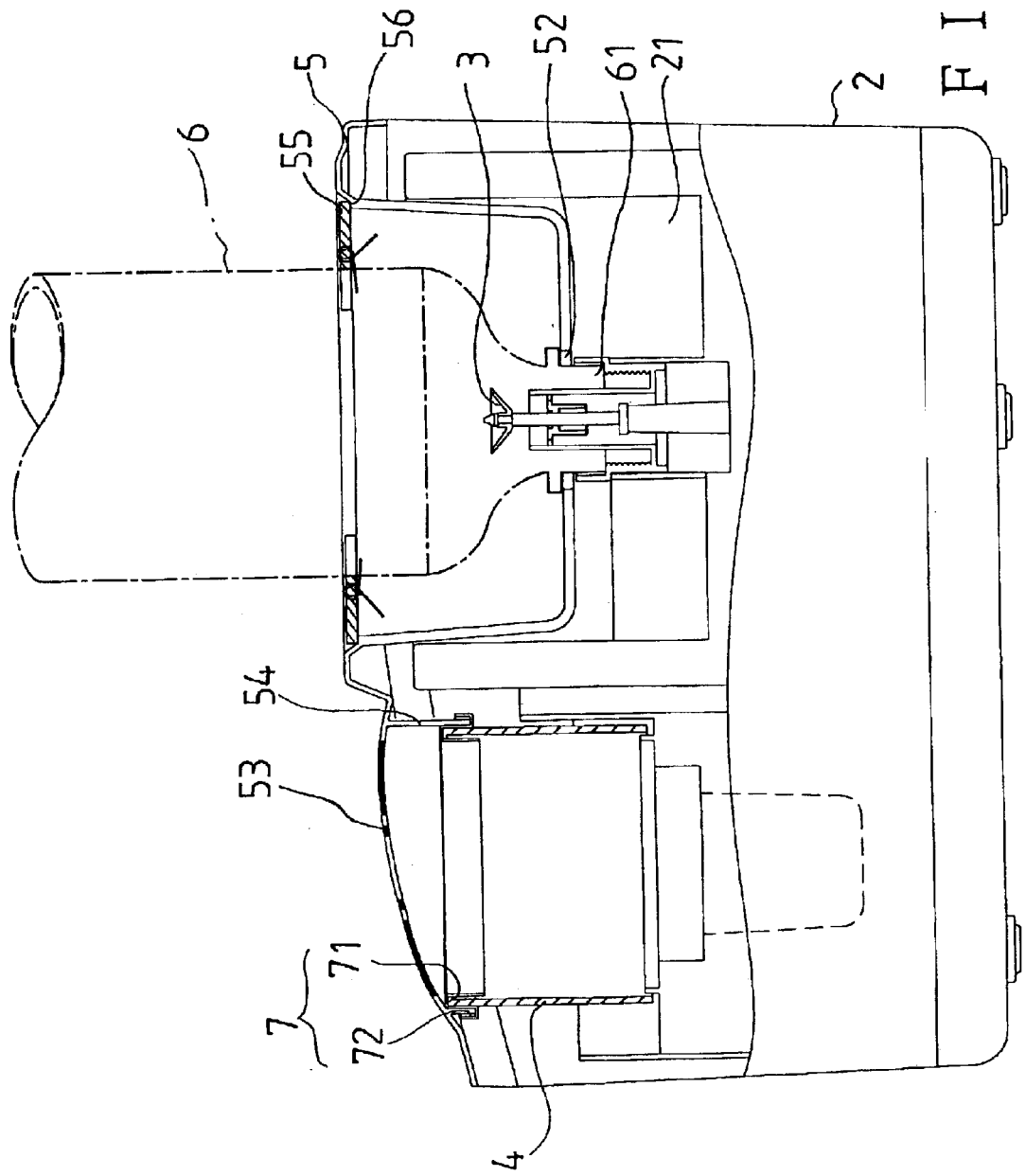
FIG. 3 is a front view of the humidifier according to the present invention.

Referring to FIGS. 1, 2, and 3, a humidifier of the present invention includes a main body 2, a valve 3, a vapor conduit 4, an upper cover 5, and a ring-shaped leakage-prevention means 7.

The main body 2 includes a heating member (not shown), a holding space 21, and a water tank in the lower section. The valve 3 is disposed in the holding space 21. A water-containing bottle 6 is connected to the valve 3 at a neck 61 thereof in an inverted position so that water can flow into the water tank via the valve 3. The conduit 4 is disposed in the main body 2 for vapor produced by the main body 2 to pass through.

The leakage prevention member 7 has several ring-shaped portions, which define inner and outer concentric annular trenches 71, and 72.

The upper cover 5 has a vapor outlet 53, and an annular holding portion, which defines a holding room 51, and which has a through hole 52 on a center of a bottom. The holding portion of the upper cover 5 has an annular inwards projecting edge 56 at an upper section thereof, and two pairs of connecting protrusions (not numbered), each of which has a pivotal hole, on upper portions of two opposite inner sides thereof.

In addition, two supporting plates 55 are provided, each of which has two opposite pivotal pins, and a concavely curved inner edge.

In combination, one of the pivotal pins of each of the supporting plates 55 is passed through a torsion spring 511, and the pivotal pins are passed into the pivotal holes of the connecting protrusions sticking inwardly of the holding room 51. And, the torsion springs 511 engage respective supporting plates 55 and corresponding connecting protrusions to exert rotary force on the supporting plates 55 so as to bias inward edges of the supporting plates 55 upwards; outward edges of the supporting plates 55 being stopped from moving down by the annular inwards projecting edge 56 therefore the torsion springs 511 can only force the supporting plates 55 to move to a horizontal position as shown in FIG. 3. The leakage prevention member 7 is closely mounted onto an upper end of the conduit 4 at the inner annular trench 71 thereof. The upper cover 5 is joined to the upper end of the main body 2 with the vapor outlet 53 being disposed right above the conduit 4, and with the annular protrusion 54 closely fitting into the outer annular trench 72 of the leakage prevention member 7.

And, the holding portion of the upper cover 5 is held in the holding space 21 of the main body 2 with the through hole 52 being right above the valve 3.

Figure 4:
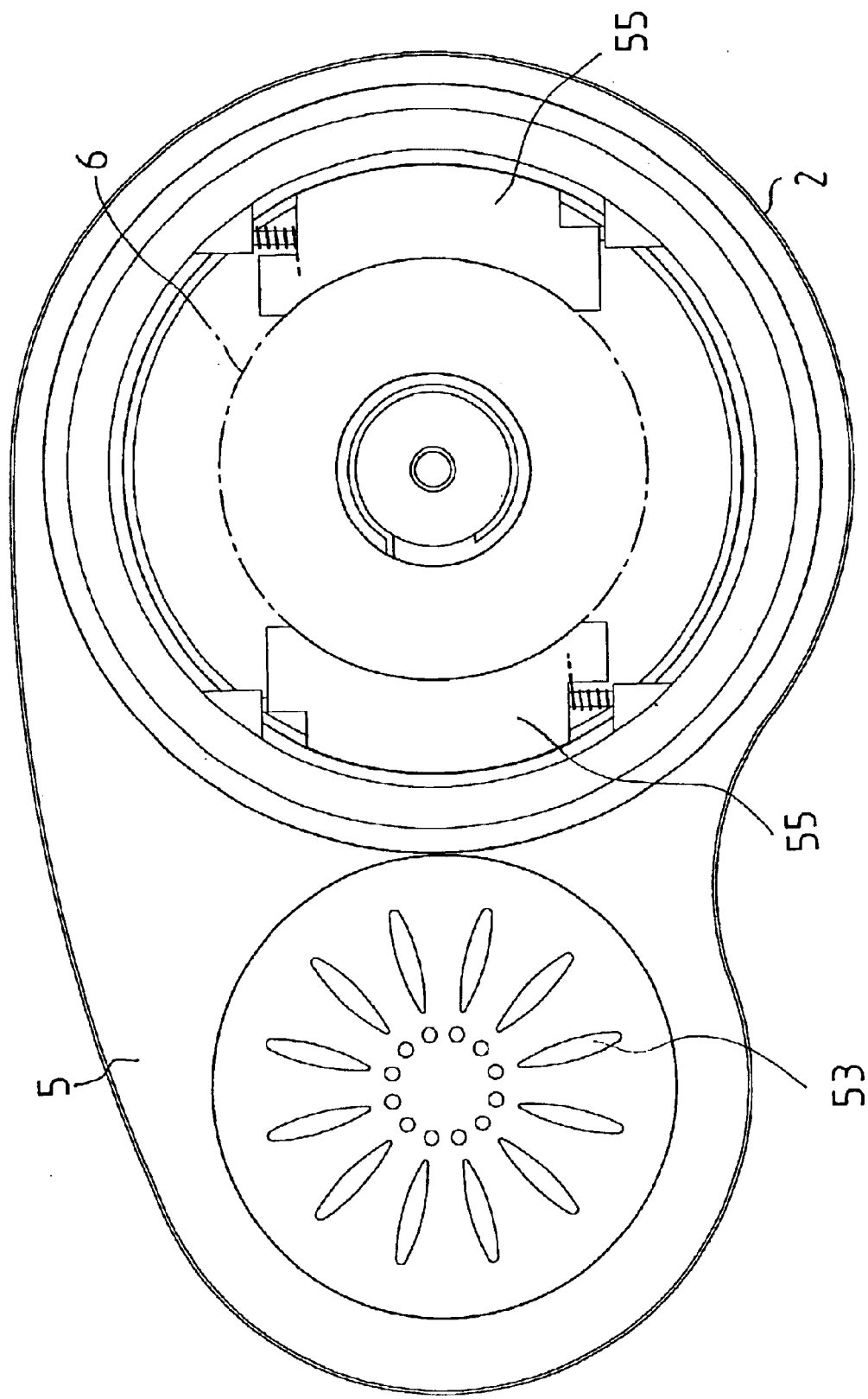
FIG. 4 is a top view of the humidifier with a water-containing bottle connected thereto according to the present invention.
Figure 5:
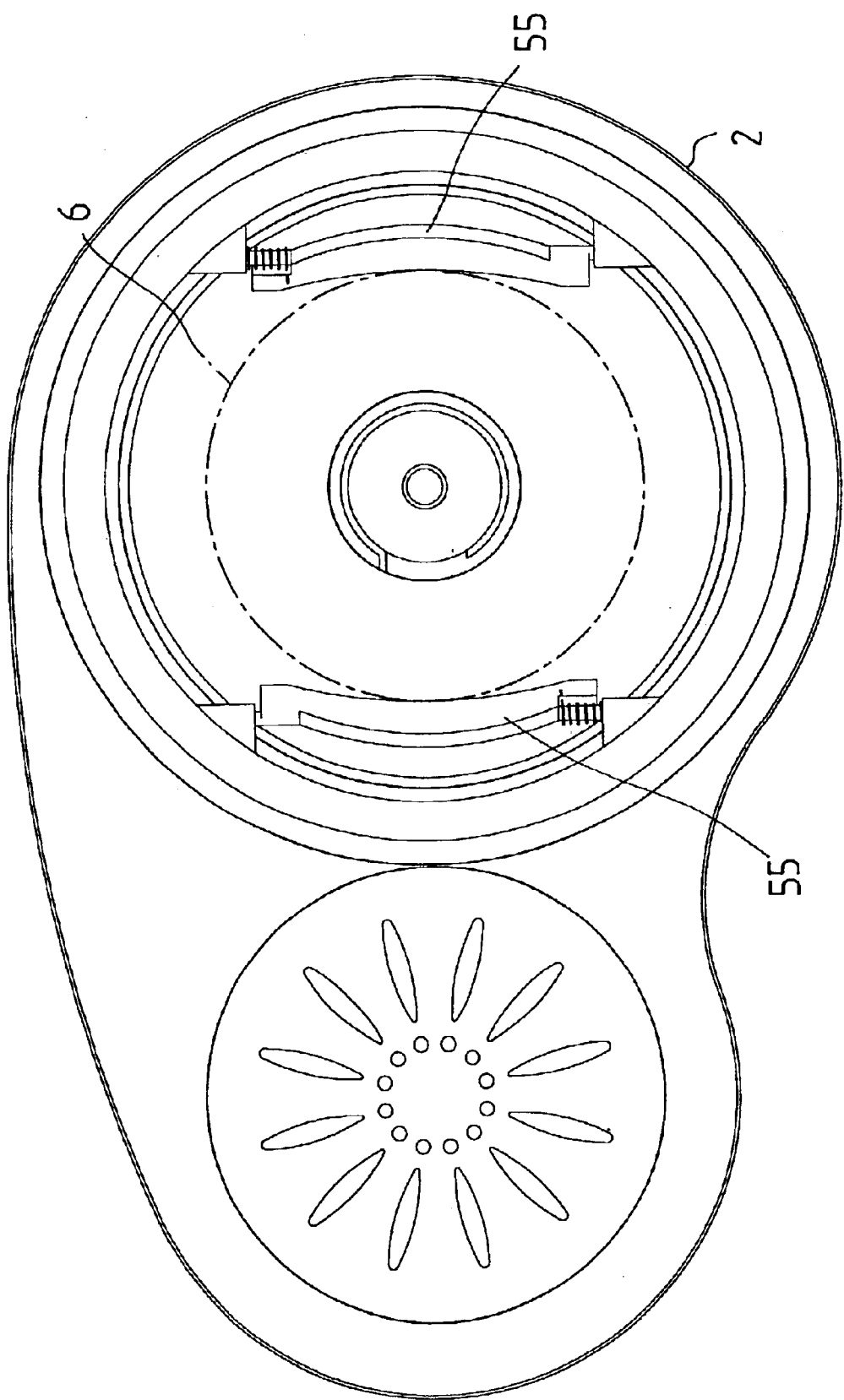
FIG. 5 is a top view of the humidifier with another water-containing bottle connected thereto according to the present invention.
Figure 6:
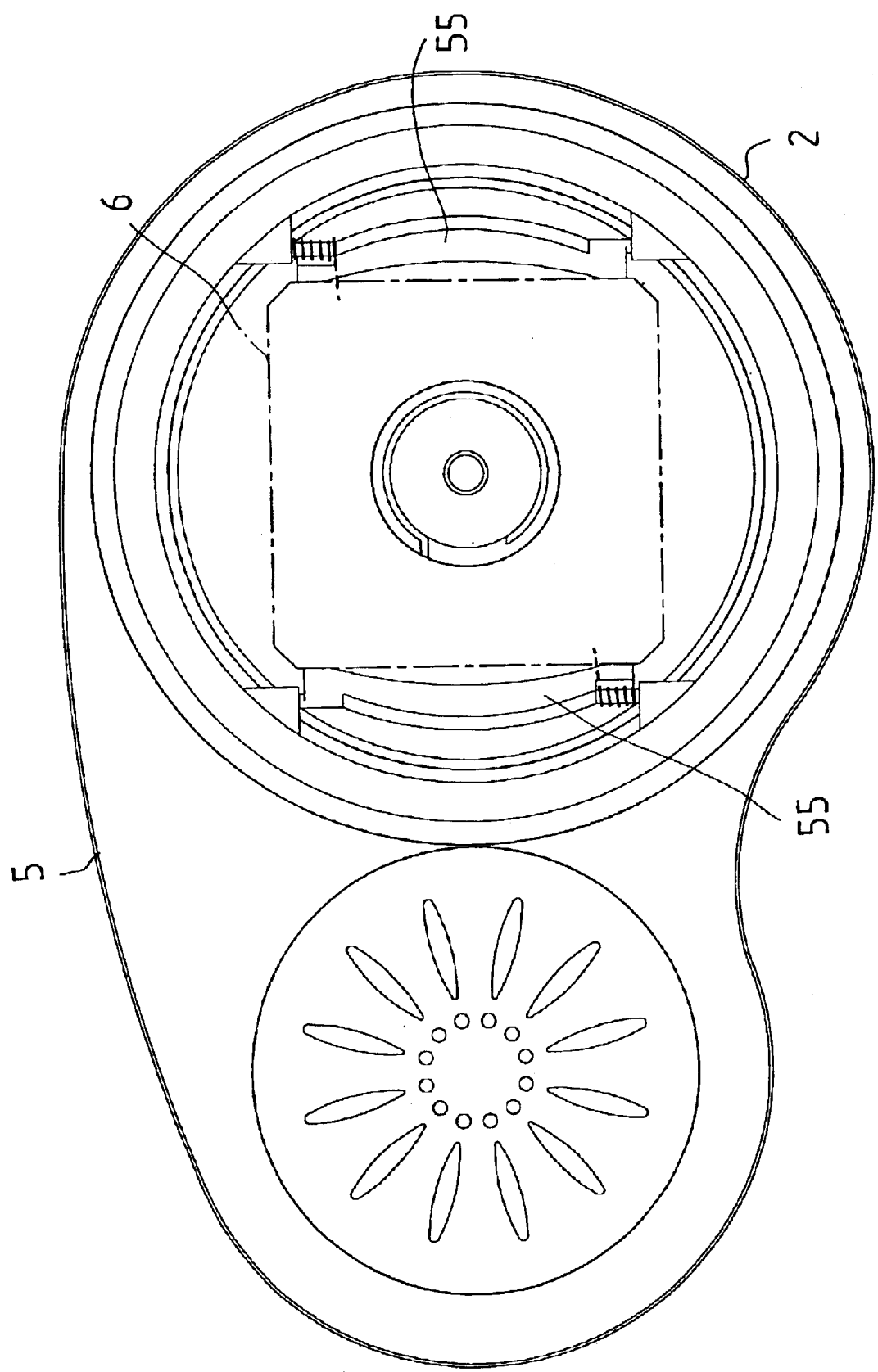
FIG. 6 is a top view of the humidifier with yet another water-containing bottle connected thereto according to the present invention; and, FIG. 7 is a side view of the humidifier and the bottle in FIG. 6.
Figure 7:
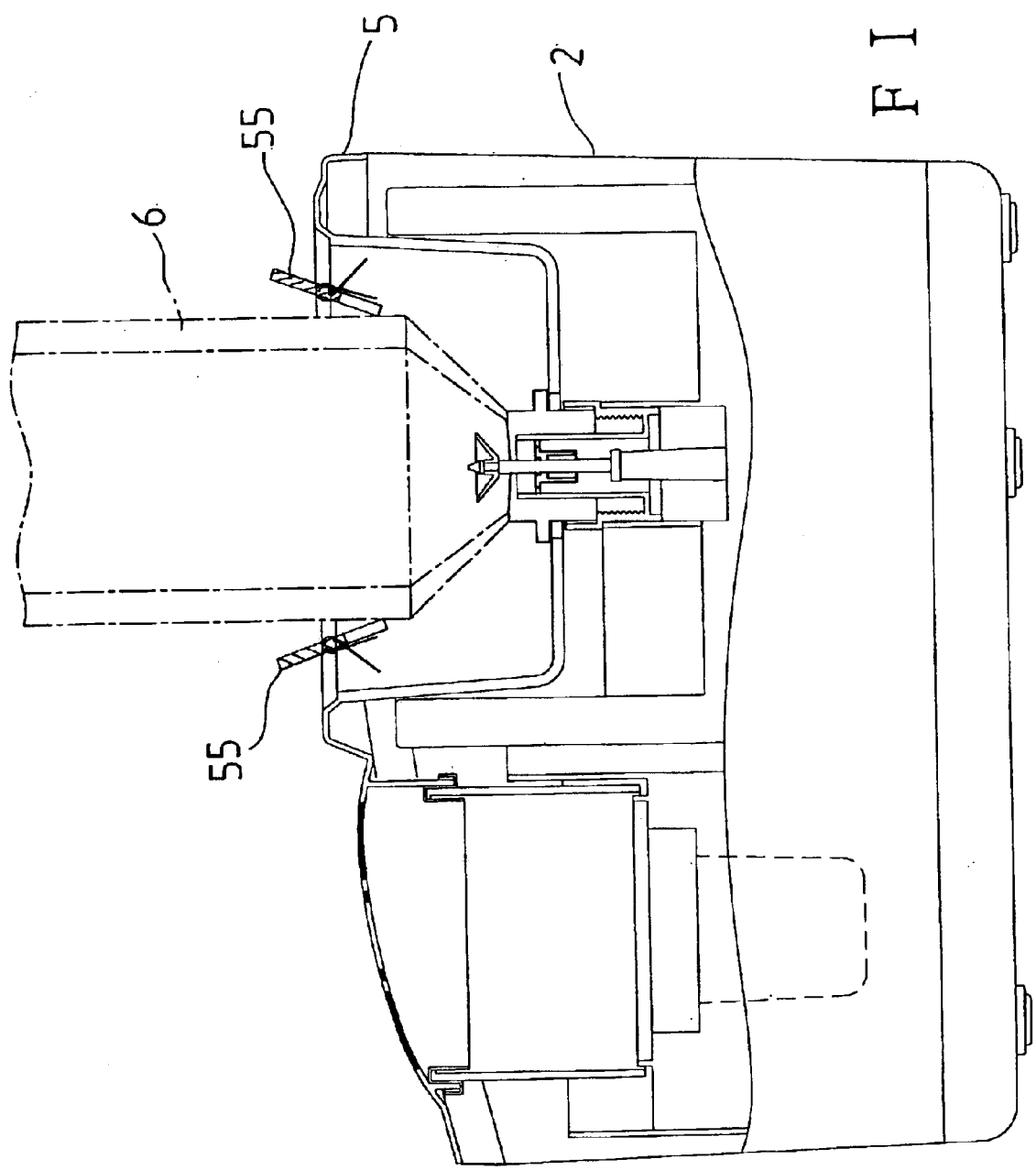

Thus, a portion of the inverted water-containing bottle 6 can be passed through between the opposite supporting plates 55, and the bottle neck 61 can be passed through the through hole 52 to be connected to the valve 3. Referring to FIGS. 4, 5, and 6, because the supporting plates 55 can pivot on the holding portion, bottles 6 having relatively big circumferences still can be passed through between the supporting plates 55; the torsion springs 511 can keep the supporting plates 55 in a sloping position after the supporting plates 55 are forced to pivot to the sloping or vertical position by bottles 6 having relatively big circumferences. In other words, the torsion springs 511 will keep the supporting plates 55 in sloping position with certain resistance if a bottle connected to the valve 3 has such a circumference that the supporting plates 55 are forced to pivot away from the usual horizontal position by the bottle. Therefore, bottles with various circumferences can be supported in a vertical position by the supporting plates 55 even if the supporting plates 55 are positioned in sloping position.

From the above description, it can be easily understood that the humidifier according to the present invention has advantages as followings:

1. Vapor is can't possibly leak through the joint between the conduit 4 and the vapor outlet 53 because of the leakage prevention means.
2. The water-containing bottle connected to the humidifier can't possibly shake or tilt due to the supporting plates. Therefore, there is no possibility of damage being caused to the valve 3 connected to the neck of a water-containing bottle by unwanted movement of the bottle.

What is claimed is:

1. An improvement on a humidifier, comprising a main body including a water-containing portion, and a valve connected to the water-containing portion; and, an upper cover joined to the main body; the upper cover having a vapor outlet disposed right above a vapor conduit of the main body; the upper cover having a holding portion disposed in a holding space of the main body with a through hole of a bottom of the holding portion being right above the valve so that a water-containing bottle in inverted position can be connected to the valve at a neck of the bottle; and, being characterized by a ring-shaped leakage prevention member joined to an upper end of the conduit and a lower annular protrusion of the vapor outlet; the leakage prevention member having a plurality of ring-shaped portions, which define inner and outer concentric annular trenches, closely fitted onto corresponding sides of the upper ends of the vapor conduit and the lower annular protrusion of the vapor outlet.

2. The improvement on a humidifier as claimed in claim 1, wherein the holding portion defines a holding room therein, and two opposite supporting plates are connected to an upper portion of an inner side of the holding portion to contact corresponding lateral sides of the bottle so that the bottle is stopped from moving sideways to a tilted position; the opposite supporting plates being up and down pivotal, and being biased towards a substantially horizontal position with torsion springs so that bottles of various circumferences can be inserted between the supporting plates, and can be stopped from moving sideways to a tilted position by means of the supporting plates; an annular inward projecting edge being formed on the inner upper portion of the holding portion to prevent corresponding edges of the supporting plates from moving past them so as to restrict pivotal movement of the supporting plates.

3. The improvement on a humidifier as claimed in claim 2, wherein two pair of connecting protrusions each having a pivotal hole are formed on the inner upper portion of the holding portion, and each of the opposite supporting plates has two opposite pins inserted into the pivotal holes of respective pairs of connecting protrusions of the holding portion, and the torsion springs connected to the supporting plates are passed around the pins.

4. The improvement on a humidifier as claimed in claim 3, wherein the supporting plates are made to have a concavely curved shape on inward edges thereof.

* * * * *